United States Patent [19]
Blumberg et al.

[11] 3,973,129
[45] Aug. 3, 1976

[54] FLUORIMETRIC APPARATUS AND METHOD FOR ANALYSIS OF BODY FLUID

[75] Inventors: William Emil Blumberg, Glen Gardner; Josef Eisinger, Bethlehem Township; Angelo Anthony Lamola, Warren, all of N.J.

[73] Assignee: Bell Telephone Laboratories, Incorporated, Murray Hill, N.J.

[22] Filed: Jan. 10, 1975

[21] Appl. No.: 540,074

[52] U.S. Cl............................ 250/461 B; 23/230 B; 23/253 R
[51] Int. Cl.².......................................... G01N 21/38
[58] Field of Search................ 250/458, 461, 461 B, 250/428, 432, 435; 23/230 B, 253 R

[56] References Cited
UNITED STATES PATENTS 3,763,374   10/1973   Tiffany et al. .................. 250/432 X
3,854,050   12/1974   Peterson et al. ................. 250/461 B Primary Examiner—Davis L. Willis
Attorney, Agent, or Firm—G. S. Indig

[57] ABSTRACT

Fluorimetric assay procedures indicative of the presence of antigens or other abnormal conditions in body fluids permit rapid, accurate screening. Extra-clinical testing is facilitated by a fluorimeter design providing for optical excitation of a totally absorbing sample and for fluorescence being detected in a direction which avoids sensing of simple reflected excitation energy. An exemplary procedure in which the sample is a drop of unprocessed blood screens for lead intoxication and iron deficiency anemia.

29 Claims, 1 Drawing Figure

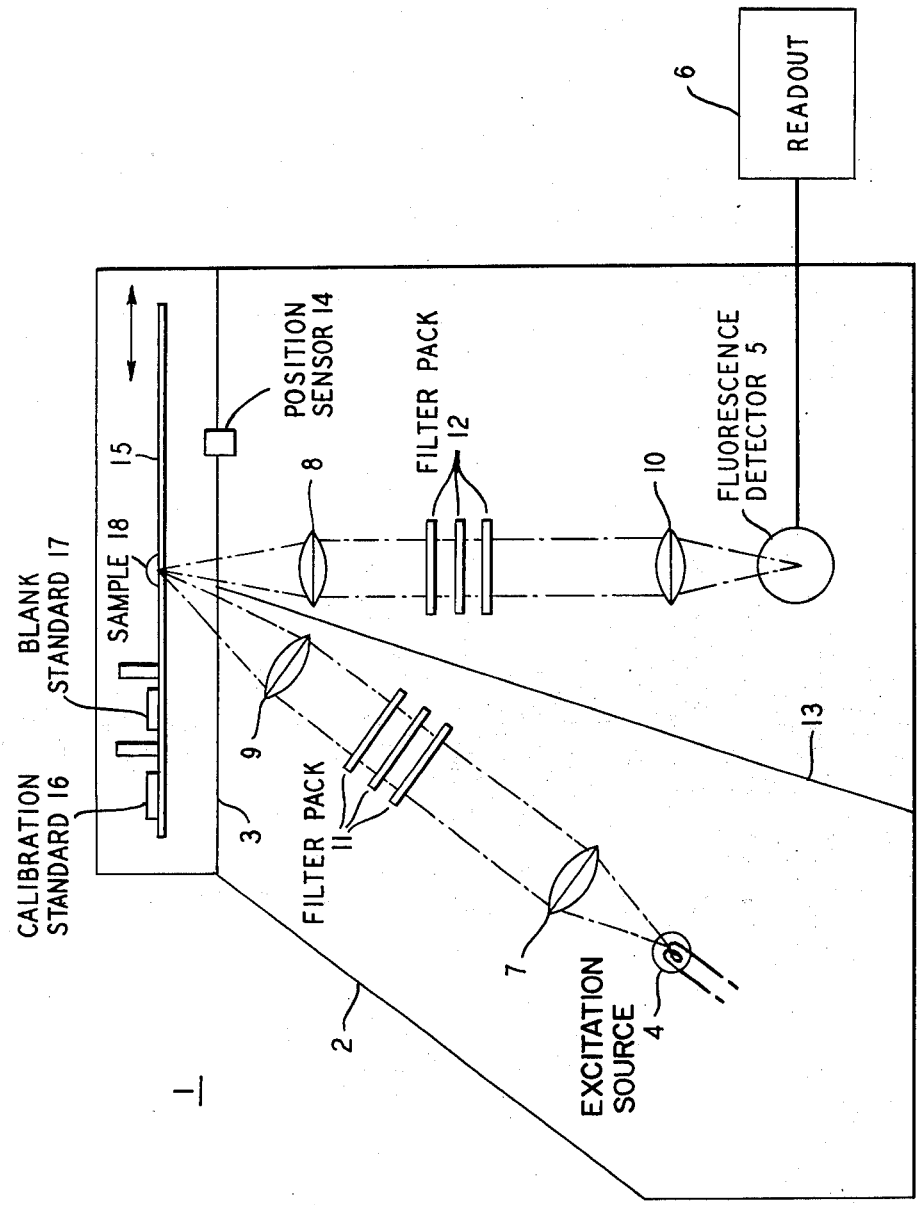

FLUORIMETRIC APPARATUS AND METHOD FOR ANALYSIS OF BODY FLUID

Background of the Invention

1. Field of the Invention

The invention is concerned with fluorimetric assay procedures for body fluids. Such fluids, which may include human blood, urine, lymph, perspiration, etc., may be processed or unprocessed and may be in liquid or solid form during analysis. Conditions which may be detected include those resulting from the presence of antigens, such as produced by bacteria, as well as intoxicants, such as lead.

2. Description of the Prior Art

It is common knowledge that the vast majority of bacterial infections, viral infections, various types of intoxication, and other human afflictions, including those due to contagious and infectious as well as congenital, diseases, may be detected, generally at an early stage, through study of blood samples and/or samples of other body fluids. Diagnostic, as well as non-diagnostic, physical examinations generally include one or more tests conducted on body fluids, such as on blood or urine. Periodic physicals may include a large number of tests conducted on blood samples, and may include, inter alia, determinations directed toward the presence, absence, or quantitative level of diverse antigens, toxic agents, enzymes, metabolites, as well as trace and other elements normally contained in the fluid under investigation. Diagnostic investigations may include procedures specifically directed to conditions suggested by the symptoms. Screening procedures of this nature, too, are valuable in times of epidemic, as well as to detect conditions arising from intoxication which may be prevalent on a regional or other basis.

An important example of the last category is concerned with the detection of lead poisoning. This form of intoxication can be permanently disabling in children and, unfortunately, is prevalent in children, particularly in urban areas. It is also an occupational hazard for workers in a variety of fields, such as, metal reclamation and demolition work. Prevalence of lead poisoning, in particular, has created a recognized need for a practical screening test to replace the atomic absorption or conventional wet chemical analytical procedures now in use. Such conventional procedures, while sufficiently sensitive and reliable, are time consuming and are quite expensive largely due to the need for experienced, highly skilled clinical personnel. Conventional analytical procedures do not lend themselves to large-scale screening for other reasons as well--notably the need for relatively large blood samples required both to increase precision and to minimize contaminating effects of lead and lead compounds found both in the air and as intentional or unintentional ingredients of surfaces contacted during processing.

Responsive to funding by a variety of organizations, e.g., the Center for Disease Control of the U.S. Department of Health, Education, and Welfare, the search for a practical screening test for lead intoxication has been extensive. Recent studies have oftentimes been directed to detection not of the toxic agent, itself, (elemental lead) but rather to measurement of some of the metabolites indicative of lead poisoning. Exemplary candidates which have been investigated are δ-aminolevulinic acid, δ-aminolevulinic acid dehydratase, and coproporphyrin (1,2). See 28, Arch. Environ. Health, 198 (1974); and 79, J. Pediatrics, 719 (1971). Protoporphyrin extractable from blood has been considered particularly promising. See 84, J. Pediatrics, 496 (1974); 51, Pediatrics, 254,280 (1973); 52, Pediatrics (Letters) 486 (1973); 81, J. Lab. Clin. Med., 932 (1973).

"Free erythrocyte protoporphyrin" (FEP) has been known for over forty years. See 12, Klin. Wschr., 586–589 (1933); and 21, Pediatrics, 40–46 (1958). It is known that FEP causes red cells to fluoresce in the red when excited with blue light. See Iron Metabolism and its Clinical Significance by A. Vanotti and A. Delachaux, New York, Grune (1949). It is known that the protoporphyrin may be extracted from the red corpuscles by the use of a variety of acidic solvents. See "Determinations of Porphyrins in Biological Materials" by Schwartz, Berg, Bossenmaier and Dinsmore in Methods of Biochemical Analysis, Vol. 8 by D. Glick (1960) pp. 253–255. Extracted protoporphyrin may be assayed by absorption spectrophotometry or by fluorimetry. Fluorescence of FEP has been utilized as a means for detecting and counting individual abnormal red cells by use of a microscope. See 24, Pediatrics, pp. 734–738 (1959). FEP, both in the cells and acid-extracted, has been suggested as a monitor of lead intoxication. See 69, Proc. Nat. Acad. Sci., 2381-2385 (1972); 8, Biochemical Med., 135–148 (1973); and 50, Pediatrics, 625–631 (1972).

In general, such analytical procedures, whether depending on fluorescence, atomic absorption, or wet or other forms of chemical analysis, have, of necessity, been performed in clinical laboratories. Precise measurement of the low concentrations of involved materials have required very careful sample preparation so that all such procedures have, in general, involved significant time delays. With few exceptions, extracted fluid samples have been forwarded to laboratories manned by highly qualified personnel and equipped with expensive and sophisticated instruments.

Fluorimetry, as regularly practiced in such assay work, has involved preparation of near-transparent cuvette samples designed for use in an instrument which provides for essentially unattenuated passage of a beam of excitation light in one direction with fluorescence being detected in a direction normal to the excitation beam. Preparation of the dilute near-transparent sample, itself, requires very precise volumetric measurement. A related method mentioned above also dependent upon fluorescence is based upon actual count of fluorescent blood cells by optical microscopy.

To date, only atomic absorption and wet chemical analytical procedures for lead, itself, have been approved by the U.S. Surgeon General for detection of lead intoxication. As discussed, such procedures are not suitable for extra-clinical use. Diagnosis or screening for other conditions are, generally, no further developed. Tests designed to establish pregnancy, to measure cholesterol level, or to identify bacterial or viral diseases, are, in general, time consuming and necessarily conducted in a laboratory.

SUMMARY OF THE INVENTION

Fluorimetric assay procedures and equipment adaptable to, but not restricted to, extra-clinical use are described. A common feature is use of a sample of a body fluid, or solids derived from a body fluid, which is totally absorbing for excitation energy. Use of such a sample with an absorption length for relevant excitation energy of a millimeter or less may minimize or eliminate altogether criticality of sample thickness. Samples may consist of unprocessed blood, urine, lymph, perspiration, etc., or may consist of fluids which are rendered fluorescent only by treatment. Treatment may include chemical reaction, coagulation, physical separation, as by centrifuging, etc. to result either in a fluid or a non-fluid sample. Apparatus of the invention provides for insertion of such a "totally absorbing" sample, generally on a rigid, transparent, horizontally disposed support, with excitation irradiation being made incident upon and fluorescence being detected from the underside of the sample--that is, from the interfacial surface at the support. Such apparatus provides both for narrow band excitation and narrow band detection of fluorescence. Overlapping portions of the excitation band and detection band are avoided generally by means of optical filter packs. False readings due to detection of reflected excitation energy are consequently minimized. Filter packs which may be fixed for specialty apparatus, or removable or adjustable for general purpose apparatus, typically consist of two or three members each, so as to define band pass regions.

"Background" level is, in preferred embodiments, maintained at a low value by two further expedients: (1) excitation beam directions and fluorescence emission directions both typically small (less than about 45° to the normal direction and with such angles designed to avoid simple reflection of excitation energy to the detection means--typically, one or the other of the two directions is essentially perpendicular to the interfacial sample surface; and (2) use of a shielding member between the excitation beam and fluorescence detection directions.

Instrument design aspects giving rise to preferred species of the inventive apparatus include: the use of a photomultiplier; readout display, perhaps digitalized; and simple means for calibration. The latter may take the form of sample holders provided with two positions in addition to that for the sample: the first carrying a non-fluorescent standard of absorption characteristic similar to that of the sample; and the second carrying a standard of known fluorescence level. Apparatus may be provided with sensors for determining standard and sample positions, and provision may be made for a "zero" position for fixing the system background level.

While excitation and emission detection bandwidths are generally defined by simple optical filter elements, other variations are contemplated. Polarizing elements may be used to sense a change in polarization of the fluorescence characteristic of a condition of concern. More sophisticated means, such as gratings or prisms, or variable interference filters, may find use in defining pass bands where more precise discrimination is desired.

While apparatus and procedures of the invention are usefully applied to an extensive class of analyses, a particular procedure deserves special comment. It has been found that fluorimetric examination of a drop of unprocessed whole blood permits rapid screening for lead intoxication. This embodiment, based on fluorescence of zinc protoporphyrin (ZPP) yields an accurate, highly precise reading at a sensitivity at least an order or magnitude below the level of lead intoxication considered dangerous in children. A fluorescence level which may be read out within a minute from the time of collection of a drop of blood produced from a single fingertip puncture appears to afford the widely sought early detection procedure for childhood lead intoxication. Since ZPP may also be simptomatic of iron deficiency anemia, screening reveals this condition as well. Closely related emission wavelengths produced by excitation of other forms of protoporphyrin may reveal instances of the congenital disease, erythropoietic protoporphria. Filter packs may be designed to include this emission wavelength as well.

BRIEF DESCRIPTION OF THE DRAWING

The FIGURE is a diagrammatical view of a fluorimeter in accordance with the invention.

DETAILED DESCRIPTION

1. The FIGURE

Apparatus depicted includes in outline design aspects of a fluorimeter suitable for extra-clinical use, although clinical use is not precluded. Fluorimeter 1 includes major housing 2, minor housing 3 for receiving sample and standards, excitation source 4, fluorescence detector 5 and display means 6. Other elements schematically depicted include excitation beam collimating means 7, fluorescence emission collimating means 8, excitation focusing means 9, fluorescence focusing means 10, band narrowing means 11 and 12, partition 13 and position sensor 14.

Illustrative of the contemplated extra-clinical design, means 7 through 10 are depicted as simple lenses, while means 11 and 12 are shown as filter packs. As discussed, means 11 and 12 may consist of fixed or changeable optical filters. In either event the minimum requirement is for elimination of the long wavelength portion of excitation from source 4 to prevent overlap with the fluorescence to be detected by means 5. Preferred design for optical filter packs results in a specifically defined band pass at each of the two positions. Means 11 results in a defined band corresponding with a suitable absorption region in the sample to be studied while means 12 results in a similarly well-defined region centered about the fluorescence wavelength of concern. Center frequencies for pass bands defined by means 11 and 12 may be 425 nanometers and 595 nanometers, respectively, (this illustration being a preferred design for screening for lead intoxication in whole blood). In more sophisticated designs, either or both of means 11 and 12 may consist of or include more specific elements, such as, gratings, prisms, or adjustable interference filters. A contemplated test which depends upon net polarization may include one or more polarizing elements. Elements included in means 11 and 12, while likely fixed, for many contemplated uses may take the form of removable packs. Apparatus provided with slots or other support members for such removable packs may be considered a general purpose instrument. Since, as described, a very large variety of uses may depend upon fluorescence labeling with one specific fluorescent molecule, a very small number of filter packs may be sufficient for a large variety of tests.

Description of the apparatus and process both in this section and elsewhere has been largely in terms of the functional portion of the excitation energy. Accordingly, it has been generally contemplated that absorption is primarily of a wavelength directly associated with fluorescence of concern. While not directly so stated, it has been tacitly assumed that fluorescence is a single photon event and with a minimum of radiationless processes. These assumptions have been elemental in discussions of, inter alia, filter packs as well as absorption distance. In fact, preferred embodiments in accordance with the invention are so directed.

Many of the samples contemplated, e.g., whole blood, are characterized by a broad absorption spectrum often extending to much shorter wavelengths than required. While some energy within this broad band may result in protein or other fluorescence which may be irrelevant to the study in progress, much of it may, through intermediate events, produce the wanted fluorescence. In certain instances relatively short wavelength fluorescence may be directly advantageous. For example, urine specimens, generally transparent in at least the lower portion of the visible spectrum, are quite absorbing at the short wavelength end of the spectrum. The general requirement of "total absorption" may, therefore, be met without use of an added opacifying agent.

Proper construction of the requirement of total absorption must take the above considerations into account. The general requirement is extremely significant in that fluorescence readings are made independent of sample size (and particularly of sample thickness in the irradiation direction). To the extent that absorbing radiation resulting in fluorescence of concern is not totally absorbed, independence of sample size is less perfect. The extent to which relevant irradiating energy is not totally absorbed is a design parameter which may be considered in terms of tolerable background signal. Ideally there is essentially no background introduced by long distance penetration of such energy. For most purposes it is considered adequate to provide for irradiating energy such that at least 90% of the energy resulting in fluorescence to be measured is in fact absorbed within the defined absorption distance of one millimeter.

Fluorescence detector 5 is, in the usual embodiment, a photomultiplier; although other detection means, perhaps depending upon pyroelectricity, photoconductivity, or other known phenomena may be substituted.

Means 6 provides for some type of readout from detector 5. It may include a printout and may be analog or digital. A preferred embodiment considered particularly suitable for mobile screening purposes provides for digital output.

As depicted, the apparatus includes a sample support 15 which may take the form of a rigid, flat transparent member, such as a microscope slide. For the arrangement shown, the sample support 15 is provided with a calibration standard 16, a blank standard 17, and a sample 18 so arranged that the two standards and the sample are irradiated in that order as the support is inserted. Positioning of support 15 may be expedited by position sensor 14. Standard 16 is a body of fluorescent material of known concentration which has similar emission properties as the fluorescent material in sample 18 to which the detector 5 is sensitive. Standard 17, a body of material of absorption properties similar to that of sample 18 but devoid of fluorescence centers, establishes a noise level for the apparatus 1.

2. Apparatus Characteristics

The apparatus is generally described in the FIGURE description. It will be recognized that it has distinguishing features adapted to its intended use generally for screening of body fluids. An important design feature— one which reduces criticality of sample size–contemplates investigation of a sample which is "totally absorbing". Accordingly, the sample, whether it be fluid–e.g., unprocessed blood, urine, etc.–or solid–e.g., precipitate or coagulum–absorbs excitation energy efficiently. For these purposes, the absorption length in the irradiation direction is, generally, 1 mm or less–i.e., the intensity of excitation peak wavelength energy is reduced to $1/e$th of its initial value–(wherein $e$ is the base of the natural logarithm system)–during traversal of 1 mm or less of sample. In the instance of whole blood, this condition is generally inherent due to the hemoglobin–i.e., the absorption distance for radiation within the visible and near UV spectra is, generally, much less than 1 mm. Where the sample is not sufficiently absorbing, material absorbing at the excitation wavelength but otherwise inert with respect to the desired conditions, may be added. So, for example, hemin may be added to a urine sample to increase absorption (e.g., for 400 nanometers wavelength radiation in screening for porphyria cutanea tarda).

Sample examination, particularly for liquid samples, is expedited by use of a rigid, flat support which is transparent both to excitation and emission wavelengths. Equipment design generally provides for irradiation of the sample, whatever its nature, by focusing the excitation beam on its under surface–that is, the sample surface in contact with the support. Focusing may be accomplished by lenses or mirrors. Filters, sometimes fixed, sometimes replaceable, are used to at least block any long wavelength portion of the excitation energy that may be detected as fluorescence. Ideally, the bandwidth of the excitation beam is restricted to a fairly narrow band centered about the desired excitation wavelength. Conventional optical filters which may define a pass band of some 10 nanometers in width are generally adequate. Fluorescence wavelength is generally separated from the excitation wavelength by an interval greater than the pass band.

Where band restrictions are critical, it is more likely to be in the path defining the detection direction. Again, optical elements are generally sufficient, at least to avoid false readings due to any reflected or scattered excitation energy. Generally, since it is contemplated that most testing will be of the screening type, it is not important to avoid closely spaced fluorescence indicative of abnormal conditions other than that under study. Where it is desired to make the reading more specific, it may be necessary to resort to the use of interference filters or diffraction gratings or other more discriminatory elements.

Apparatus design is otherwise such as to minimize "noise"–i.e., detection output which is unrelated to the fluorescence centers to be detected. Fluorimeters of the invention are arranged with detection direction being non-coincident with any simple reflection direction for the excitation beam. In general, one of the two directions is perpendicular to the underside of the sample, while the other is within the solid cone of angles of a maximum of about 45° from the perpendicular. Filter or other elements are desirably perpendicular to excitation and emission detection directions, again, to avoid unwanted reflection and are inserted in collimated beams to avoid change in focus when additional members are inserted. Finally, in a preferred apparatus design, a dividing plate intermediate the two directions is provided. This plate, which may make solid contact with the sample support and may bisect the angle separating the two directions, may be of absorbing or nonreflective material.

In the apparatus depicted, the sample holder has provision for a standard of the absorption qualities of the sample but with no fluorescence–here designated the "blank standard"–and a "calibration standard" with absorption properties also like the sample under investigation but with a known level of fluorescence. Calibration and allowance for apparatus background may readily be accomplished by comparison of detection levels for the two standards with that of the sample. Assuming a photomultiplier or other detector with current output proportional to fluorescence level, a meaningful reading is the value of the ratio R defined as:

$$R = \frac{I_A - I_B}{I_C - I_B},$$

where $I_A$, $I_B$, and $I_C$ are the photomultiplier currents for sample, blank standard, and calibration standard respectively. A preferred embodiment yields this reading as a digital display within a very short interval (a few seconds or less) after the standards and sample have been exposed.

3. Procedures

A. Testing for Fluorescence Which Results as an Inherent Consequence of the Disorder This procedure contemplates no necessary processing of blood, urine, blister fluid, etc., although inert absorbant material may be added to meet the total absorption excitation requirement if a quantitative determination is required. A prime example is fluorescence resulting from the creation of centers in whole blood due to lead intoxication or iron deficiency anemia. In heme synthesis, complexing of iron with protoporphyrin is ordinarily induced by the enzyme ferrochelatase. Conditions which interfere with formation of iron protoporphyrin results in the kinetically preferred zinc protoporphyrin complex. A condition which causes this abnormal and harmful reaction is lead intoxication in which lead inhibits the function of the enzyme, rendering it relatively inactive. Iron deficiency may result in the formation of the same zinc complex. Zinc protoporphyrin (ZPP), unlike the normal iron protoporphyrin, is fluorescent at about 595 nanometers wavelength when excited by 425 nanometers excitation. A somewhat more unusual disorder, the congenital condition resulting in excess protoporphyrin, known as erythropoietic protoporphyria, also results in fluorescence, however, at an emission wavelength of about 620 nanometers. The fluorescence associated with excess protoporphyrin may be separated out by use of an interference filter or diffraction grating. For usual screening purposes, however, there is no objection to the use of a band pass of sufficient breadth to include fluorescence from this source. Response generally results in an output which is essentially linear with ZPP concentration from a level of about 5 micrograms ZPP/100 milliliters of whole blood to a level of at least 200 micrograms ZPP/100 milliliters. The minimum ZPP level of significance for detection of lead poisoning is from 40 to 90 microgram/100 milliliters. (The lower level is significant primarily in children.) The value of 200 is well in excess of any value needed for screening of lead intoxication or iron deficiency anemia. Independence with respect to sample thickness is strikingly evidenced by the fact that the test procedure of the Example has been repeated with air-dried blood with no significant change in reading.

A second example, again utilizing a drop of unprocessed whole blood, may be specifically directed toward the detection of fluorescent porphyrins due, for example, to erythropoietic protoporphyria (EPP) or porphyria cutanea tarda. Such conditions, both congenital, result, in the first instance, in red cell protoporphyrin, and, in the second instance, in serum coproporphyrin. All such porphyrins may be detected in whole blood using an excitation filter pack or other selection means which defines an excitation beam centering about 400 nanometers wavelength. Emission generally centers about 620 nanometers wavelength.

B. Tests in which Fluorescent Centers May Be Selectively Attached to an Antigen or Antibody or Other Resultant Agent Indicative of a Disorder A general category of test in this class involves addition of a bacterium or virus to a body fluid which is being screened for a disorder resulting from the same bacterium or virus. This addition results in attack of the added agent by an antibody, presence of which results from prior introduction of the bacterium or virus (in general, this addition is required, since the antigenic source is rapidly attacked by any of the relatively large number of antibodies generated by initial infection). Further processing involves the removal of the combined antigen-antibody–perhaps by centrifuging or other mechanical separation; and treatment of any separated solid matter (including any antigen-antibody couple present) with a specific antihuman globulin antibody which is labeled with a fluorescent molecule or other fluorescent matter (the specific reagent is available from pharmaceutical companies as the refined product resulting from injection of an appropriate human antibody into a lower animal). Thereafter, mechanical separation brings down any coupled (antigen-antibody)-(fluorescent labeled antihuman globulin antibody) complex and examination of either the pellet (the solid matter produced upon separation) or of a suspension of such solid matter involves use of a detection band centering about the fluorescence of the label.

The above procedure may serve as a test for syphilis. In accordance with the general procedure, serum or whole blood is mixed with treponema pallidum antigen and is permitted to stand for a period of a few minutes to permit attack of the bacterium by any treponemal antibody. The mixture is centrifuged and the pellet is rinsed with an appropriate agent (phosphatebuffered saline solution). A solution of fluorescein labeled antihuman globulin antibody is added and the mixture is resuspended, perhaps in the same kind of saline solution. After incubation, the sample is again centrifuged and the resulting pellet is again washed. The solid matter or, alternatively, a suspension of the solid matter, is treated as the sample in apparatus such as that depicted in the FIGURE. Detected fluorescence at the fluorescence line of about 520 nanometers is a positive test for syphilis. Excitation may center about 480 nanometers. Calibration and background levels are set, as in the general description, with appropriate standards–perhaps uninfected serum for the blank standard and serum of known antitreponemal antibody content as the calibration standard.

This and other procedures requiring labeling may utilize any of a variety of fluorescent materials, such as 7-chloro-4-nitrobenzo-2-oxa-1,3-diazole, 5-dimethylamino napthalene-1-sulfonyl chloride, rhodamine isothiocyanate, 4-phenylspiro [fura-2(3H),1' phthalan]-3,3'-dione. Labeling is standard clinical practice and such practice may be followed in practicing inventive procedures. Reference to appropriate labeling procedure with some indication of excitation and emission lines is set forth in a number of references–e.g., W. D. Dandleker and A. J. Portmann, in "Excited States of Proteins and Nucleic Acids", ed. R. F. Steiner and I. Weinryb, Plenum Press, New York, N.Y., 1971, pp. 199–262. Procedures in accordance with category B are effectively utilized in the detection of any bacterial or viral infection for which the appropriate bacterial or viral antibody is available. Antihuman globulin antibodies may be labeled as described without affecting their ability to form the desired couple. Procedures of this category rely on the fact that the fluorescence labeled antihuman globulin antibody is soluble in a variety of media from which precipitation may be brought about after coupling with the human antibody-antigen pair.

C. Detection of Fluorescence Resulting from Direct Reaction of a Reagent with the Agent To be Detected This type of procedure may entail simple addition of reactant to the otherwise unprocessed body fluid. As in other categories requiring processing, quantitative measurement of added material is generally not critical–the only requirement being that there be sufficient quantity to result in assigned fluorescence to each relevant agent unit.

One example of such a direct reaction is the addition of a reagent which reacts with the agent to be detected and whose fluorescent properties are altered as a result of this specific reaction. The change in fluorescent properties may take the form of an increased quantum yield of fluorescence, a change in fluorescence polarization or a change in the fluorescence spectrum.

D. Measurement of Enzyme Activity by Addition of an Appropriate Agent as in C.

Measurement of such activity is generally timedependent so that the incubation interval must be taken into account. A variety of variations is apparent. Any body fluid, human or lower animal, process or unprocessed, may serve as the specimen. Fluorescence may be inherent or the result of treatment. It may be associated with an unwanted agent (in which event mere presence above the noise level is significant) or with an agent normally found in the body fluid (in which event quantitative measure is of greater significance).

Discussion has been largely in terms of body fluids; generally, human body fluids as processed or unprocessed. Procedures of the invention are, of course, applicable to investigation of fluids of other living organisms. Such procedures may be valuably performed, for example, in the early detection of porphyria, of consequence in cattle herds.

3. Examples

The following example was selected at random from a series of screening tests conducted on juvenile volunteers. Screening was for lead intoxication. Apparatus was, in general outline, that described in conjunction with the FIGURE. A whole blood specimen consisting of a drop of whole blood taken by finger puncture was utilized. The excitation source was a 50 watt incandescent lamp with a filter pack consisting of two plan filters and one interference filter defining a pass band of approximately 390 nanometers to 430 nanometers for the excitation beam. A similar pack also consisting of three glass filters, was used to define a pass band of from 550 nanometers to 700 nanometers for detected fluorescence. Detection was by a 10 stage photomultiplier whose sensitivity extends from the visible region out to 700 nanometers. The sample holder was provided with a blank standard and calibration standard, as described, the one consisting of simulated whole blood with no fluorescence centers in the prescribed bandwidth and the other consisting of such standard with known concentration of fluorescence centers at 595 nanometers. A digital reading of 1100 in units of microgram ZPP/100 ml whole blood was well above the accepted level requiring hospitalization for juvenile lead poisoning. A blood sample from the same subject was analyzed for lead content by a conventional clinical atomic absorption method. The clinical analysis showed close correlation with a level of lead 95 micrograms/100 ml whole blood. (The relation of ZPP to blood lead level is given by log ZPP ($\mu$g/100 ml) = 0.52 + 0.0027 Pb ($\mu$g/100 ml).)

What is claimed is:

1. Fluorimeter for investigation of a sample derived from a body fluid comprising excitation means for producing a beam of irradiating energy of spectral content including energy which is absorbed by such sample to produce fluorescence, presence and/or intensity of which is indicative of a condition under study and detection means including a detector for detecting such radiation characterized in that:
    1. the said sample is supported by support means which is essentially transparent to a spectral portion contained within the excitation beam resulting in the said fluorescence;
    2. said excitation means emits a beam directed to the underside of the said sample;
    3. the said sample has an absorption length of a maximum of one millimeter in the direction of the said excitation beam for the said spectral portion, absorption length being defined as traversal distance within the sample through which incident energy is reduced to 1/eth of its incident value, wherein e is the base of the natural logarithm system;
    4. the spectral content of said excitation beam is such that at least 90% of the contained quantum energy absorbed to produce such fluorescence meets the recited absorption length requirement;
    5. a detection means is so disposed as to detect fluorescence emanating from the underside of the said sample;
    6. both said excitation beam direction and the detection direction defining the direction of the detector relative to the sample are within the solid cone defined by an angle of 45° from a direction normal to the underside of the said sample.
2. Fluorimeter of claim 1 in which the excitation beam means includes a spectral narrowing means for reducing intensity of spectral content approaching the center wavelength of the said fluorescence.
3. Fluorimeter of claim 2 in which the spectral narrowing means includes at least one filter for lessening intensity of wavelengths within ten nanometers of the said fluorescence center wavelength.

4. Fluorimeter of claim 1 in which the said detection means is provided with detection spectral narrowing means for changing the spectral content of energy incident upon the detector.

5. Fluorimeter of claim 4 in which the said detection spectral narrowing includes at least one element for lessening the intensity of wavelengths which are substantially shorter than the said fluorescence center wavelength.

6. Fluorimeter of claim 1 including calibration means consisting of a calibration standard having an absorption length for irradiating excitation beam energy as defined in claim 1 and with known concentration of fluorescence centers emitting the said fluorescence which is indicative of a condition under study.

7. Fluorimeter of claim 6 including a blank standard of absorption characteristics similar to that of the said sample but containing essentially no fluorescence centers emitting the said fluorescence which is indicative of a condition under study.

8. Fluorimeter of claim 7 including computing means for calibrating the output signal from the said detector and also provided with display means for displaying such calibrated signal.

9. The fluorimeter of claim 8 in which the said display means provides for a digitized display.

10. The fluorimeter of claim 1 in which the said sample is chemically unprocessed.

11. The fluorimeter of claim 10 in which the said sample is fluid.

12. The fluorimeter of claim 11 in which the said sample is whole blood.

13. The fluorimeter of claim 12 in which the condition under study results in fluorescence of a porphyrin.

14. Fluorimeter for investigation of a sample of whole blood comprising excitation means for producing a beam of irradiating energy of spectral content including energy which is absorbed by such sample to produce fluorescence of zinc protoporphyrin, presence and/or intensity of which is indicative of a condition under study and detection means including a detector for detecting such radiation characterized in that:
1. the said sample is supported by support means which is essentially transparent to a spectral portion contained within the excitation beam resulting in the said fluorescence;
2. said excitation means emits a beam directed to the underside of the said sample;
3. the said sample has an absorption length of a maximum of one millimeter in the direction of the said excitation beam for the said spectral portion, absorption length being defined as traversal distance within the sample through which incident energy is reduced to 1/eth of its incident value, wherein e is the base of the natural logarithm system;
4. the spectral content of said excitation beam is such that at least 90% of the contained quantum energy absorbed to produce such fluorescence meets the recited absorption length requirement;
5. a detection means is so disposed as to detect fluorescence emanating from the underside of the said sample;
6. both said excitation beam direction and the detection direction defining the direction of the detector relative to the sample are within the solid cone defined by an angle of 45° from a direction normal to the underside of the said sample.

15. The fluorimeter of claim 14 in which the excitation beam has a significant spectral content with a center wavelength of approximately 425 nanometers.

16. Process for the fluorimetric investigation of a sample of whole blood in accordance with which the said sample is irradiated by a beam of excitation energy of substantial spectral content at a wavelength of about 425 nanometers wherein at least a portion excites fluorescence indicative of presence and/or quantity of zinc protoporphyrin characterized in that:
1. the said excitation beam illuminates the underside of the said sample;
2. fluorescence is detected by a detector positioned under the said sample;
3. both the direction of the excitation beam and the detection are within the solid cone defined by a direction which is 45° to the direction normal to the underside of the said sample;
4. the said sample has an absorption length of a maximum of one millimeter for at least 90% of the spectral content of the said excitation beam which excites fluorescence, and
5. fluorescence is detected by a detector having an electrical output which is readout in the form of a display.

17. Process for the fluorimetric investigation of a sample derived from a body fluid in accordance with which the said sample is irradiated by a beam of excitation energy of such spectral content that at least a portion excites fluorescence indicative of presence and/or quantity of an agent within such body fluid characterized in that (1) the said excitation beam illuminates the underside of the said sample, (2) fluorescence is detected by a detector positioned under the said sample, (3) both the direction of the excitation beam and the detection are within the solid cone defined by a direction which is 45° to the direction normal to the underside of the said sample, (4) the said sample has an absorption length of a maximum of one millimeter for at least 90% of the spectral content of the said excitation beam which excites fluorescence, and (5) fluorescence is detected by a detector having an electrical output which is read out in the form of a display.

18. Process of claim 17 in which the said sample is chemically unprocessed body fluid.

19. Process of claim 18 in which the said sample is whole blood, in which the excitation beam has a substantial spectral content at a wavelength of about 425 nanometers and in that the fluorescence is a porphyrin fluorescence.

20. Process of claim 17 in which excitation beam path and detection path both include spectral narrowing means for minimizing spectral overlap between the excitation energy illuminating the said sample and the energy detected.

21. Process of claim 20 in which each said spectral narrowing means includes at least one optical filter.

22. Process of claim 21 in which each path includes a filter pack, each such pack defining a passband.

23. Process of claim 22 in which the passband defined for the excitation beam path centers about a wavelength of approximately 425 nanometers.

24. Process of claim 17 in which the said sample is chemically processed.

25. Process of claim 24 in which processing includes addition of an addition agent which imparts fluorescence to the said sample.

26. Process of claim 25 in which processing includes addition of an antigen-containing agent.

27. Process of claim 26 in which the addition agent includes a fluorescence-labeled antihuman globulin antibody.

28. Process of claim 27 in which treatment of the said sample comprises a first addition of an antigen-containing agent and a second addition of a fluorescence-labeled antihuman globulin antibody.

29. Process of claim 28 in which the said antigen-containing agent is a bacterium or virus.

* * * * *

UNITED STATES PATENT AND TRADEMARK OFFICE
CERTIFICATE OF CORRECTION

PATENT NO. : 3,973,129

DATED : August 3, 1976

INVENTOR(S) : William Emil Blumberg, Josef Eisinger and Angelo Anthony Lamola

It is certified that error appears in the above-identified patent and that said Letters Patent are hereby corrected as shown below:

In the specification, Column 2, line 1, "79" should be in dark type and "J. Pediatrics" should be in italics; line 3, "84" should be in dark type and "J. Pediatrics" should be in italics; line 4, "51 and 52" should be in dark type and "Pediatrics" should be in italics; lines 4-5, "Pediatrics" should be in italics; line 5, "J. Lab. Clin. Med." should be in italics; line 8, "Klin. Wschr." should be in italics; line 9, "21" should be in dark type and "Pediatrics" should be in italics; lines 11-12, "Iron Metabolism and its Clinical Significance" should be in italics; lines 17-18, "Methods of Biochemical Analysis" should be in italics; line 23, "24" should be in dark type and "Pediatrics" should be in italics; line 26, "69" should be in dark type and "2385" should be in light type and "Proc. Nat. Acad. Sci." should be in italics; line 27, "8 and 50" should be in dark type and "Biochemical Med." should be in italics; line 28, "Pediatrics" should be in italics. Column 3, line 27, close parentheses after "45 o". Column 4, line 2, change "simptomatic" to --symptomatic--.

Signed and Sealed this sixteenth Day of August 1977

[SEAL]

Attest:

RUTH C. MASON
*Attesting Officer*

C. MARSHALL DANN
*Commissioner of Patents and Trademark*